US011733140B2

(12) United States Patent
Gu

(10) Patent No.: US 11,733,140 B2
(45) Date of Patent: Aug. 22, 2023

(54) APPARATUS AND METHOD FOR MEASURING WATER CONTENT PROFILES, INTERFACIAL LEVELS, THICKNESSES AND TENSIONS OF MULTIPHASE DISPERSIONS

(71) Applicant: Guoxing Gu, Edmonton (CA)

(72) Inventor: Guoxing Gu, Edmonton (CA)

( * ) Notice: Subject to any disclaimer, the term of this patent is extended or adjusted under 35 U.S.C. 154(b) by 217 days.

(21) Appl. No.: 17/112,662

(22) Filed: Dec. 4, 2020

(65) Prior Publication Data

US 2021/0255079 A1 Aug. 19, 2021

Related U.S. Application Data

(60) Provisional application No. 62/970,710, filed on Feb. 6, 2020.

(51) Int. Cl.
*G01N 13/02* (2006.01)
*G01N 1/44* (2006.01)
(Continued)

(52) U.S. Cl.
CPC .............. *G01N 13/02* (2013.01); *G01N 1/44* (2013.01); *G01N 33/28* (2013.01);
(Continued)

(58) Field of Classification Search
CPC .............. G01N 33/2823; G01N 33/28; G01N 33/2847; G01N 1/44; G01N 13/02;
(Continued)

(56) References Cited

U.S. PATENT DOCUMENTS 4,545,125 A * 10/1985 Rogers .................... B65G 47/26
73/52
5,589,649 A * 12/1996 Brinker ..................... B01L 7/00
219/385
(Continued)

OTHER PUBLICATIONS

Okamura et al.; Development of a 128-channel multi-water-sampling system for underwater platforms and its application to chemical and biological monitoring; Dec. 2013; Methods in Oceanography, vol. 8, pp. 75-90. (Year: 2013).*
(Continued)

*Primary Examiner* — Daniel J Colilla
(74) *Attorney, Agent, or Firm* — Bennett Jones LLP

(57) ABSTRACT

An apparatus and method for simultaneously measuring water content profiles, surface/interfacial levels, thicknesses and tensions of multiphase dispersions, such as dispersions with water dispersed in produced oils, crude oils, various fuels, distillates, lubricants, paints and polymers, or reversed dispersions with these organic components dispersed in water. The apparatus with 1-16 channels, namely multi-channel scanning water analyzer (MCSWA) and/or tensiometer, comprising a motorized precision vertical stage with multiple capacitive sensors, a heating system with multiple heating cells for keeping the respective sample bottles, and a data acquisition system, where the capacitive sensors can be precisely controlled via a computer to dip into the samples at a preset scanning velocity and the capacitances of the sensors are continuously measured by the data acquisition system. The measured sensor capacitances are used to derive water content profiles, surface/interfacial levels, interfacial thicknesses and surface/interfacial tensions of the respective samples. The apparatus is a good tool for R&D scientists to select chemicals efficiently and can provide reliable data for engineering design and product quality assurance.

11 Claims, 16 Drawing Sheets

(51) Int. Cl.
*G01N 33/28* (2006.01)
*G01N 33/32* (2006.01)

(52) U.S. Cl.
CPC ..... *G01N 33/2847* (2013.01); *G01N 33/2888* (2013.01); *G01N 33/32* (2013.01)

(58) Field of Classification Search
CPC ............... G01N 33/2888; G01N 27/22; G01N 33/1833; G01N 13/1886
USPC .................................. 73/64.55, 64.48, 64.56
See application file for complete search history.

(56) References Cited

U.S. PATENT DOCUMENTS

| | | | |
|---|---|---|---|
| 5,777,483 A * | 7/1998 | Bailey | G01N 27/221 |
| | | | 324/686 |
| 8,511,148 B2 * | 8/2013 | Fetvedt | B01F 27/806 |
| | | | 73/864.91 |
| 2016/0041286 A1 * | 2/2016 | Sinha | E21B 49/087 |
| | | | 73/152.32 |
| 2016/0231460 A1 * | 8/2016 | Pearl, Jr. | G02B 6/10 |

OTHER PUBLICATIONS

Aslam et al.; A High Resolution Capacitive Sensing System for the Measurement of Water Content in Crude Oil; Jun. 25, 2014; Department of Electrical and Electronic Engineering, Sensors Journal; vol. 14, issue 7. (Year: 2014).*

* cited by examiner

APPARATUS AND METHOD FOR MEASURING WATER CONTENT PROFILES, INTERFACIAL LEVELS, THICKNESSES AND TENSIONS OF MULTIPHASE DISPERSIONS

FIELD OF THE INVENTION

This specification includes materials in common with a provisional patent application 62/970,710 filed on Feb. 6, 2020 with the same inventor as this application. This application includes some additional information in relation to a method for measuring surface/interfacial tensions using the same apparatus that was developed for measuring water content profiles, surface/interfacial levels and thicknesses of multiphase dispersions, such as dispersions with water dispersed in produced oils, crude oils, various fuels, distillates, lubricants, paints and polymers or reversed dispersions with these organic components dispersed in water, broadening applications of the apparatus.

BACKGROUND

A produced oil is a mixture of water, oil and solids in any oil production facilities. The produced oil is commonly stabilized by natural surface active agents and requires intensive chemical and physical treatments to separate water and solids from oil. Knowing water distribution, phase boundaries and interfacial thicknesses in any process vessel are crucial to both operation engineers and R&D scientists as well as management personnel's. Water and basic sediment (BS&W) content in oil must be well controlled to be less than 0.5% for acceptance of downstream pipeline transportation. Enhanced oil recovery technologies are extensively used everywhere, they heavily rely on chemical addition to improve oil recovery, but added chemicals adversely impact treatment of produced oils. The added chemicals help oil to liberate from surface of oil sands and then form a dispersion either in the form of oil-in-water (O/W) or water-in-oil (W/O) emulsion. The emulsified dispersions must be treated for oil products. Currently, the water distribution analysis and phase boundary identification are carried out in lab first followed by field confirmation. Phase boundary visual identification is very difficult for heavy oils due to their dark, viscous and sticky nature. This lab-intensive work is a must in both engineering and operation stages to figure out the best types of chemicals, dosages, chemical working temperature and adding procedure as well as chemical adding location in a line of production and separation vessels, e.g. well heads, well lines, gas and free water knock out vessels, oil/water separation vessels and oil purification vessels. Water analysis is also important in quality assurance in various downstream oil products (such as fuels and lubricants) and other industry's products (such as paints and polymers). Phase boundaries or interfacial levels can be used to evaluate how much clean oil, emulsion, rag layer and aqueous phases available in a process vessel. Interfacial thicknesses provide additional information for evaluating effectiveness of added chemicals.

To do water analysis in a lab, firstly, oil samples are taken in bulks at fields and sub-sampled in lab into multiple testing bottles for water distribution and phase boundary identification; secondly, chemicals are added to the testing samples and mixed thoroughly on a shaker followed by keeping the samples in a thermostat or water bath at a desired temperature for a certain duration to allow phase separation; thirdly, a few small amount of samples are withdrawn using a syringe from each sample bottle at different vertical levels for subsequent water or BS&W analysis; finally, the water or BS&W analysis can be done using one or in combination of the three methods: centrifuge [such as ASTM D1796-11 (2016), ASTM D4007-11(2016), ASTM D2709-16], distillation (such as ASTM D95 and ASTM D4006) and Karl Fischer titration [such as ASTM D4928-12(2018), ASTM D6304-16, ASTM D4017, ASTM D6869-17, ASTM E203-16, ASTM E1064-16].

Both centrifuge method and distillation method involve use of one of toxic and flammable diluents: such as toluene, xylene, petroleum naphtha, petroleum spirit and other petroleum distillates having a boiling point range of 90-210° C. There is a strong health and environmental safety concern on using such toxic and flammable diluents. The Karl Fischer titration method also involves use of toxic Karl Fisher reagents, which consist of an alcohol (ethanol or diethylene glycol monoethyl ether), a base (imidazole or pyridine), sulfur dioxide ($SO_2$) and iodine ($I_2$). All of the three methods can only provide water or BS&W content at one or a few vertical levels of testing sample in a bottle. The centrifuge method requires at least 5 ml sample, taking 3 samples from 3 vertical levels of a 150-200 ml bottle is operable, however, taking 5 samples is extremely difficult, meaning that it is very limited for water distribution and phase boundary identification. The distillation method requires a large volume of sample, e.g. 25 ml for water content less than 10% by volume, and 200 ml for water content less than 1% by volume, meaning that it is not suitable for water distribution analysis of sample in a 150-200 ml sample bottle. Only the Karl Fisher titration method is suitable for water distribution analysis and phase boundary identification as it just requires a small amount of sample.

Surface/interfacial energies play a very important role in various industrial processes, such as mineral separation, oil sands separation, waste water treatment, pulp and paper making, surface coating, painting, etc. Surface and interfacial properties can be conventionally measured using drop methods (sessile drop method and pendant drop method) and probe methods (Du Noüy ring method, Du Noüy-Padday rod method and Wilhelmy plate method). Measurement principles are well described elsewhere, such as cscscientific.com, kruss-scientific.com, rheologylab.com, sinterface.com, etc.

Hence, the object of present invention is to develop a highly desirable apparatus and method that measures water content continuously and provides water content profiles, surface/interfacial levels (or phase boundaries), interfacial thicknesses and surface/interfacial tensions of multiphase dispersions using the apparatus.

SUMMARY OF THE INVENTION

A apparatus and method is provided for simultaneously measuring water content profiles, surface/interfacial levels and interfacial thicknesses of multiphase dispersions, such as the dispersions with water dispersed in produced oils, crude oils, various fuels, distillates, lubricants, paints and polymers, or the reversed dispersions with these organic components dispersed in water. Surface or interfacial tension can also be measured thereafter using the same apparatus once the surface/interfacial levels are identified. The apparatus with 1-16 channels, namely multi-channel scanning water analyzer (MCSWA) and/or multi-channel tensiometer, comprising a motorized precision vertical stage with multiple capacitive sensors, a heating system with multiple heating cells for keeping multiple sample bottles and a data acquisition system, where the capacitive sensors can be precisely controlled via a computer to dip into the samples at a preset scanning velocity and the capacitances of the sensors are continuously measured by the data acquisition system. The measured sensor capacitances are then used to derive water content profiles, surface/interfacial levels, interfacial thicknesses and surface/interfacial tensions of the respective samples for chemical screening, engineering design and production quality assurance.

DETAILED DESCRIPTION OF PREFERRED EMBODIMENTS

Figure 1:
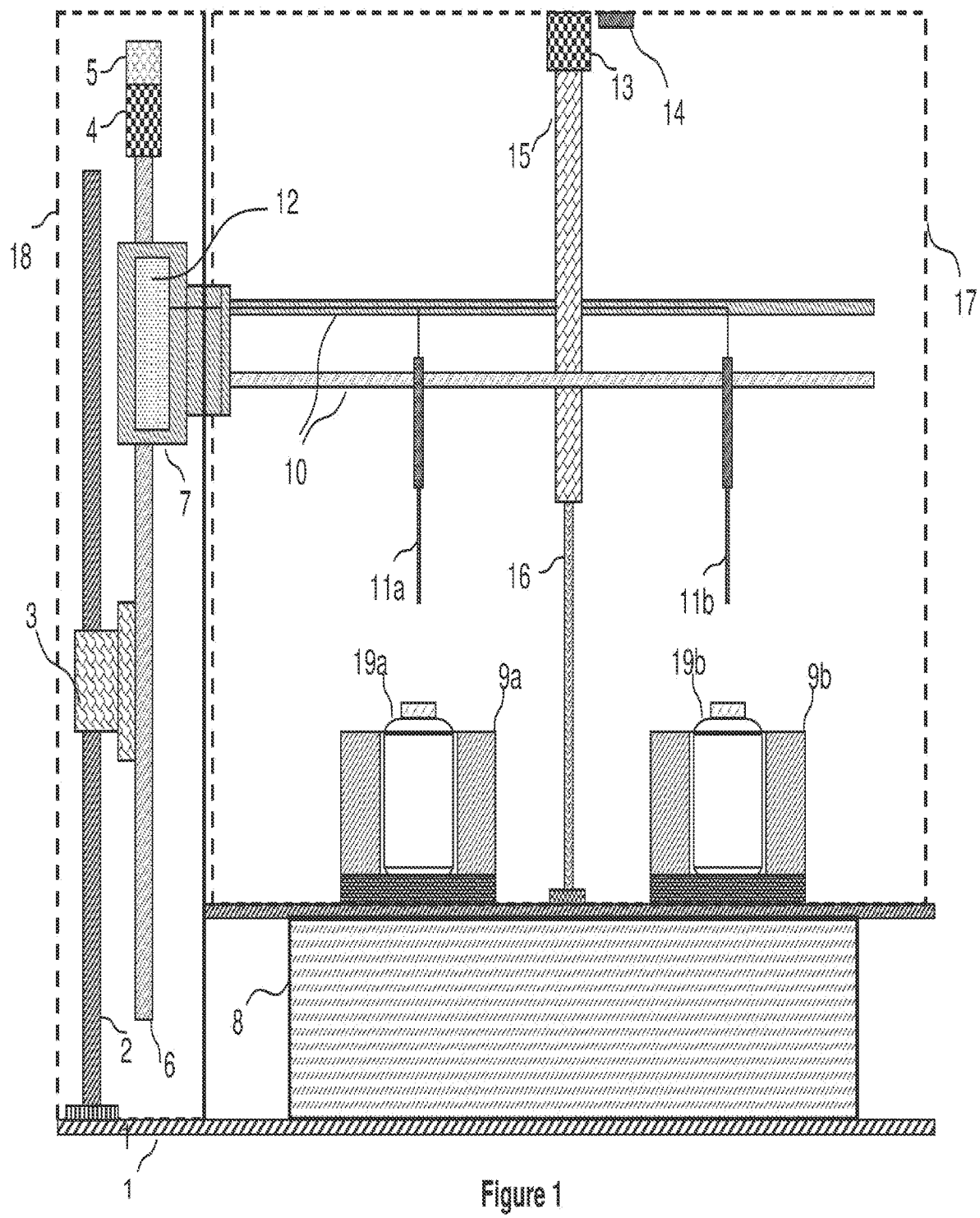
FIG. 1 is a schematic illustration of a 4-channel scanning water analyzer/tensiometer.

The present invention is described below with reference to FIG. 1, which is a schematic illustration of a 4-channel scanning water analyzer, comprising a support station having a base frame (1), a post (2) and a clamp (3), a motorized vertical linear stage integrating a motor (4), a motor controller (5) and a motor travel guide (6) and a moving unit (7), a heating system having a heating control box (8) and multiple heating cells (9a, 9b, 9c and 9d, not all shown in FIG. 1), a sensor holder manifest (10) holding multiple sensors (11a, 11b, 11c and 11d, not all shown in FIG. 1), a data acquisition unit (12) attached to the vertical stage's moving unit (7) so that the data acquisition unit can move with the stage's moving unit together, a front enclosure (17) that can be manual or motorized, a fixed rear enclosure (18) and multiple glass bottles (19a, 19b, 19c and 19d, not all shown in FIG. 1) and an integrated driver for controlling the vertical stage's precise movement and data acquisition as well as data processing. For the motorized enclosure, there are a motor (13), a motor controller (14), a cylinder (15), an extendable/retractable moving rod (16) and the enclosure (17). Each data acquisition unit (12) has 4 channels. The multi-channel can be any even number from 2-16, of course, it can also be single channel as well. Each channel requires a heating cell, a respective sensor and a glass bottle with testing sample. Multiple data acquisition units can be used for an apparatus with number of channels greater than 4 and can be directly connected to a computer via multiple USB ports or via a USB hub. The motor controllers (5) and (14) can also be connected directly to the computer either via USB ports or the USB hub. It is preferable to use a USB 2.0 or 3.0 hub to integrate all controllers into one connection point to the computer. It would be a good option to use a low voltage (5-12 V) motor (13) for the front enclosure (17) so that the enclosure can be operated by either a power supply or a battery set. The use of a battery set can avoid a hanging power cable for the motor (13) that move the enclosure up and down. The fixed rear enclosure (18) is detachable for easy electrical maintenance. The heating control box has a temperature controller, a fuse, a power switch, a solid state relay, a power distribution unit connecting to multiple cartridge heaters.

Figure 2:
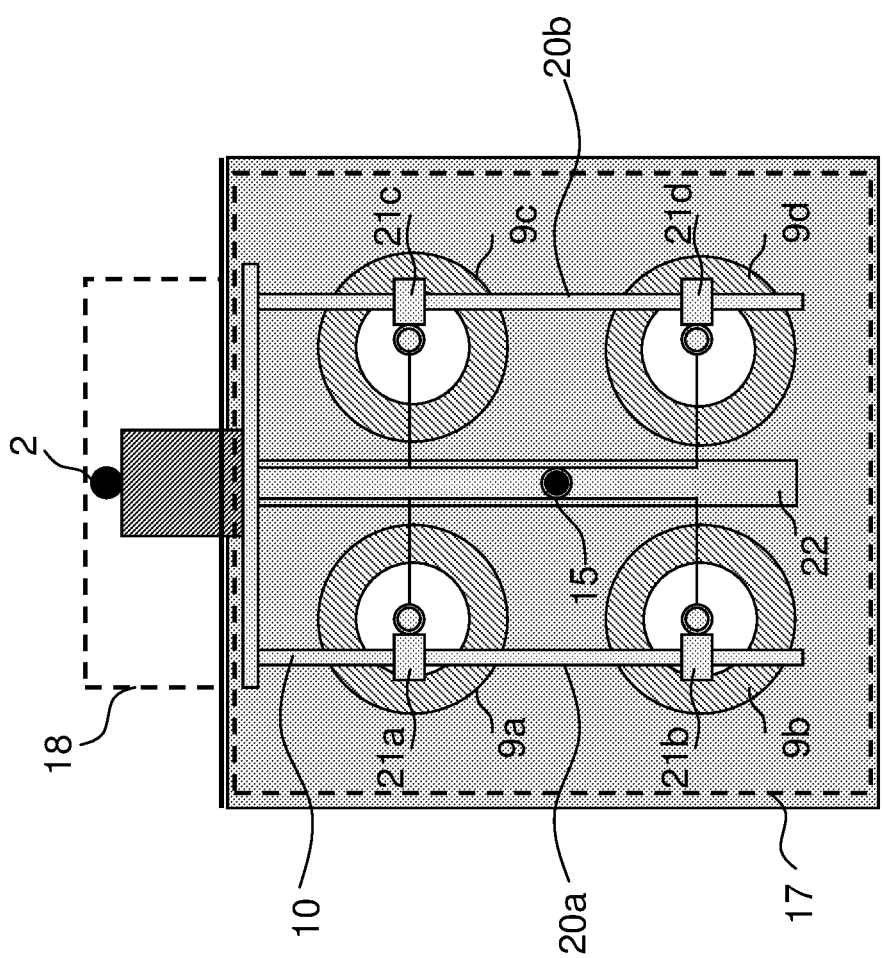
FIG. 2 is a schematic illustration of top view of a 4-channel scanning water analyzer/tensiometer.

Referring to FIG. 2, which is a schematic illustration of top view of a 4-channel scanning water analyzer/tensiometer, having 4 heating cells (9a, 9b, 9c and 9d) arranged center-symmetrically. The sensor holder manifest (10) has 2 round bars or tubes (20a and 20b) working as guides for positioning the 4 sensors precisely. The 4 sensors are hung on the guides via 4 pieces of 90° adapters (21a, 21b, 21c and 21d). The electrical wires connecting each sensor are shielded and enclosed in a wire channel metal box (22) to its data acquisition unit (12). The electrical wires connecting each sensor can also be tied to and routed along the sensor holder (10) directly to the data acquisition unit (12). To minimize noises the data acquisition unit (12), the sensor holder manifest (10) with sensors (11a, 11b, 11c and 11d) and the electrical wire channel metal box (22) are all attached to the motor's moving unit (7) and move together in a whole.

Figure 3:
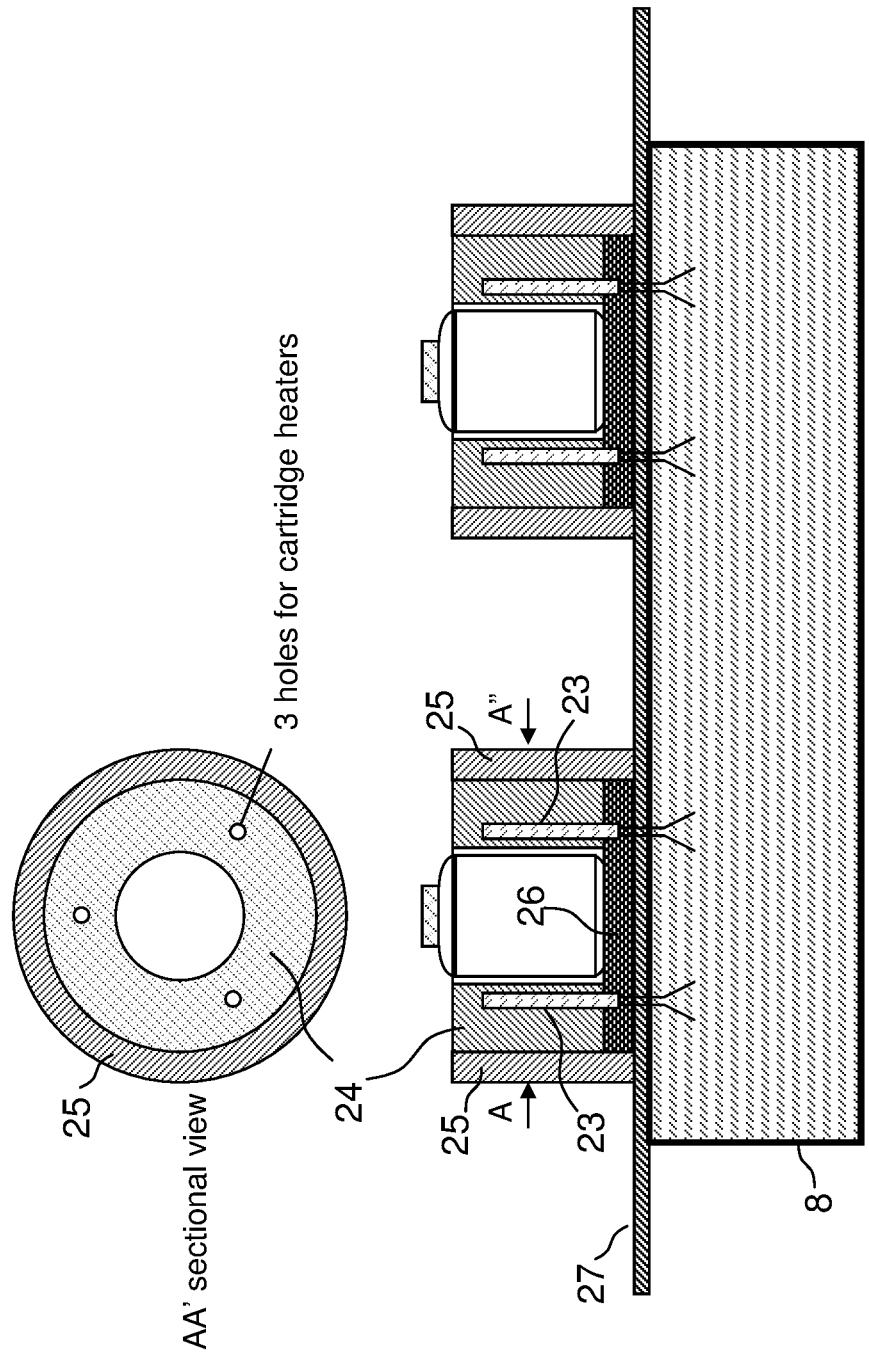
FIG. 3 is a sectional illustration of the heating system.

Referring to FIG. 3, which is a sectional illustration of the heating system having a heating control box (8) and multiple heating cells (9a, 9b, 9c and 9d, not all shown in FIG. 3). Each heating cell has 3 cartridge heaters (23) inserted in its wall of the metal ring (24) surrounded by insulation materials (25 around and 26 bottom), the insulated heating cell is then sitting on a base plate (27) made of also one of the insulation materials, which can be fiberglass, mica, mineral fiber, refractory cement, etc., preferably mineral fiber and mica.

Figure 4:
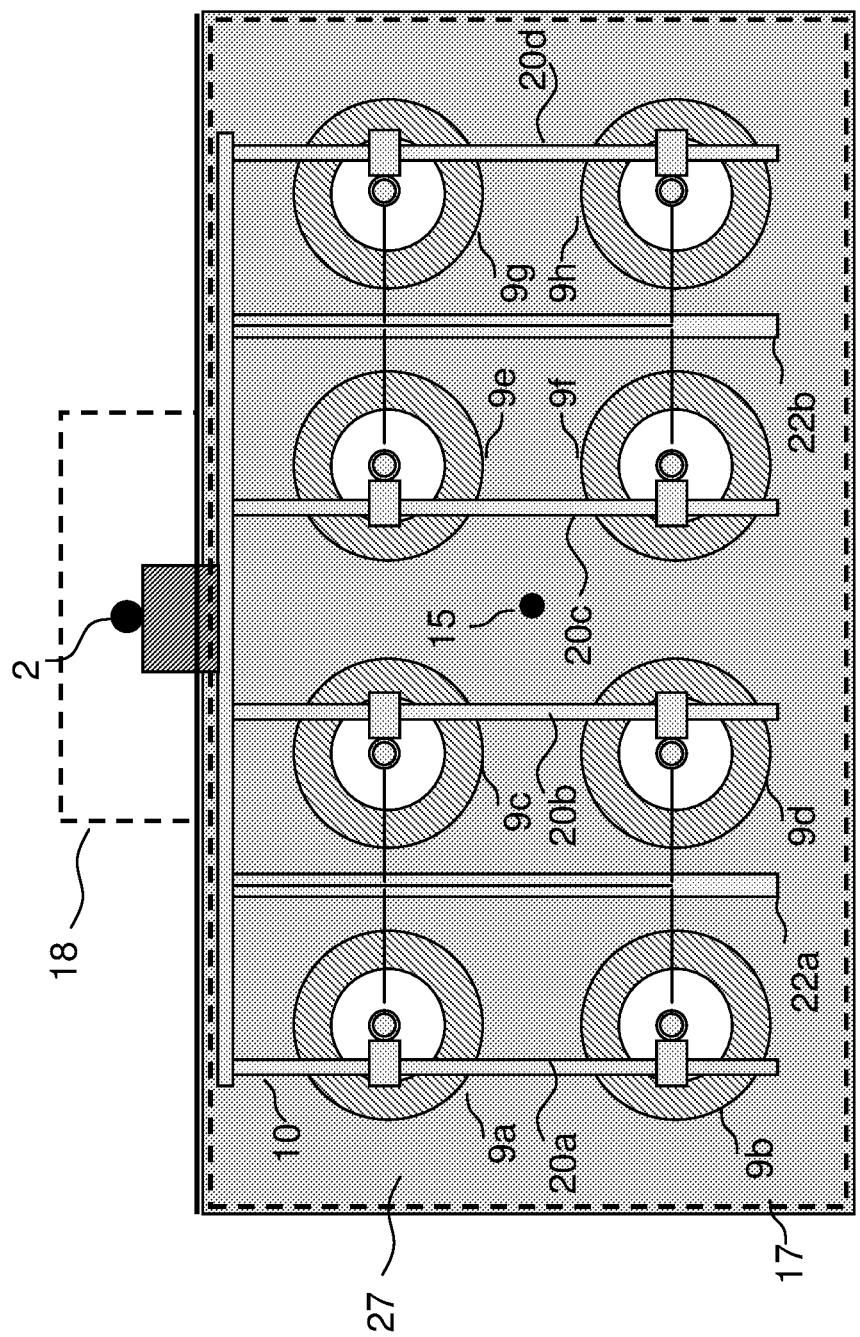
FIG. 4 is a schematic illustration of top view of a 8-channel scanning water analyzer/tensiometer.

Referring to FIG. 4, which is a schematic illustration of top view of a 8-channel scanning water analyzer/tensiometer, having 8 heating cells that are grouped into 2 sets, one set (9a, 9b, 9c, and 9d) is on the left side and another set (9e, 9f, 9g and 9h) is on the right side of the centered cylinder (15). The sensor holder manifest (10) has 4 round bars or tubes, two (20a and 20b) working as guides for positioning precisely the 4 sensors on the left side and other two (20c and 20d) working as guides for positioning precisely the 4 sensors on the right side. The electrical wires connecting all sensors on the left side are shielded and enclosed in a wire channel metal box (22*a*) to its data acquisition unit (12*a*, not shown in FIG. 4) and all sensors on the right side are shielded and enclosed in a wire channel metal box (22*b*) to its data acquisition unit (12*b*, not shown in FIG. 4). The electrical wires connecting each sensor can also be tied to and routed along the sensor holder manifest (10) directly to the data acquisition unit (12).

Figure 5:
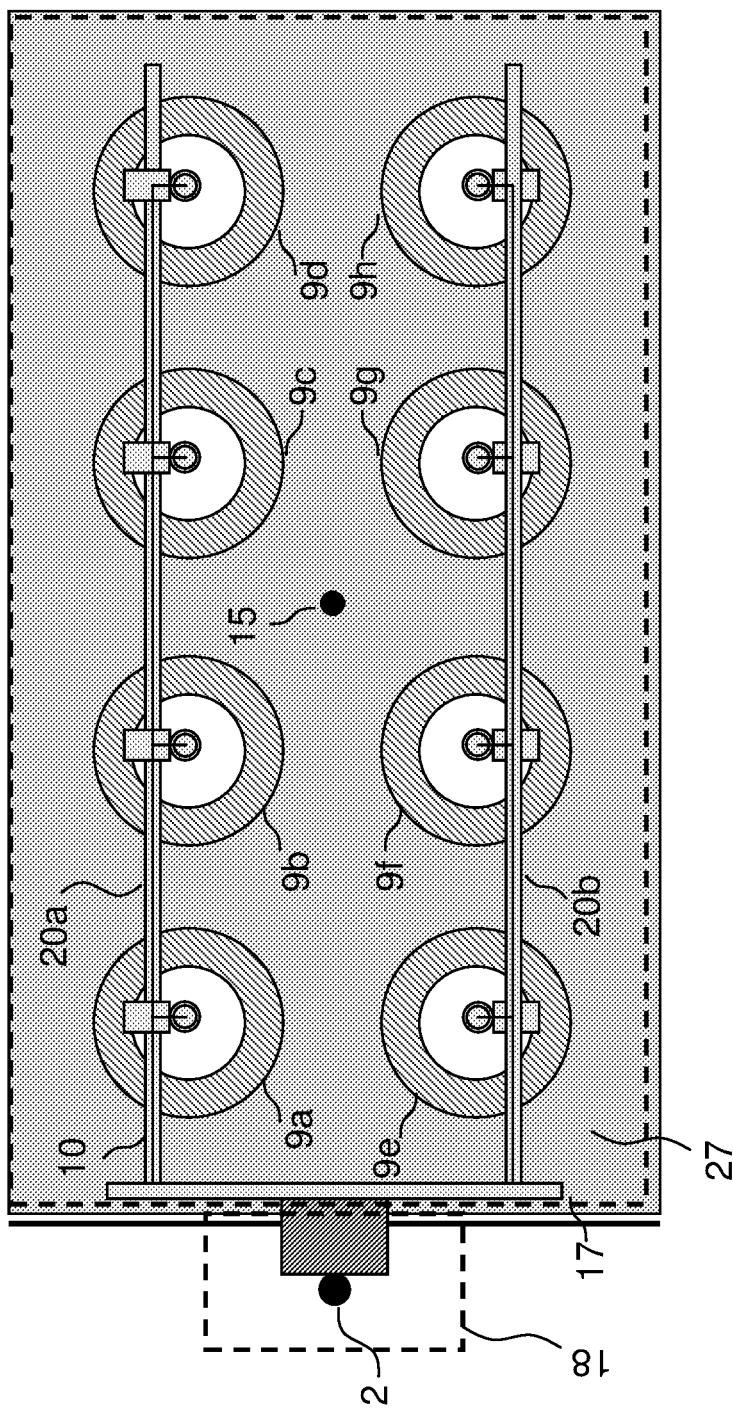
FIG. 5 is an alternative schematic illustration of top view of a 8-channel scanning water analyzer/tensiometer.

Referring to FIG. 5, which is an alternative schematic illustration of top view of a 8-channel scanning water analyzer/tensiometer, having 8 heating cells that are grouped into 2 sets, one set (9*a*, 9*b*, 9*c*, and 9*d*) is on the top side and another set (9*e*, 9*f*, 9*g* and 9*h*) is on the bottom side of the centered cylinder (15). The sensor holder manifest (10) has 2 round bars or tubes (20*a* and 20*b*) working as guides for positioning precisely the 8 sensors. The electrical wires connecting each sensor are tied to and routed along the sensor holder manifest (10) directly to the data acquisition unit (12).

Figure 6:
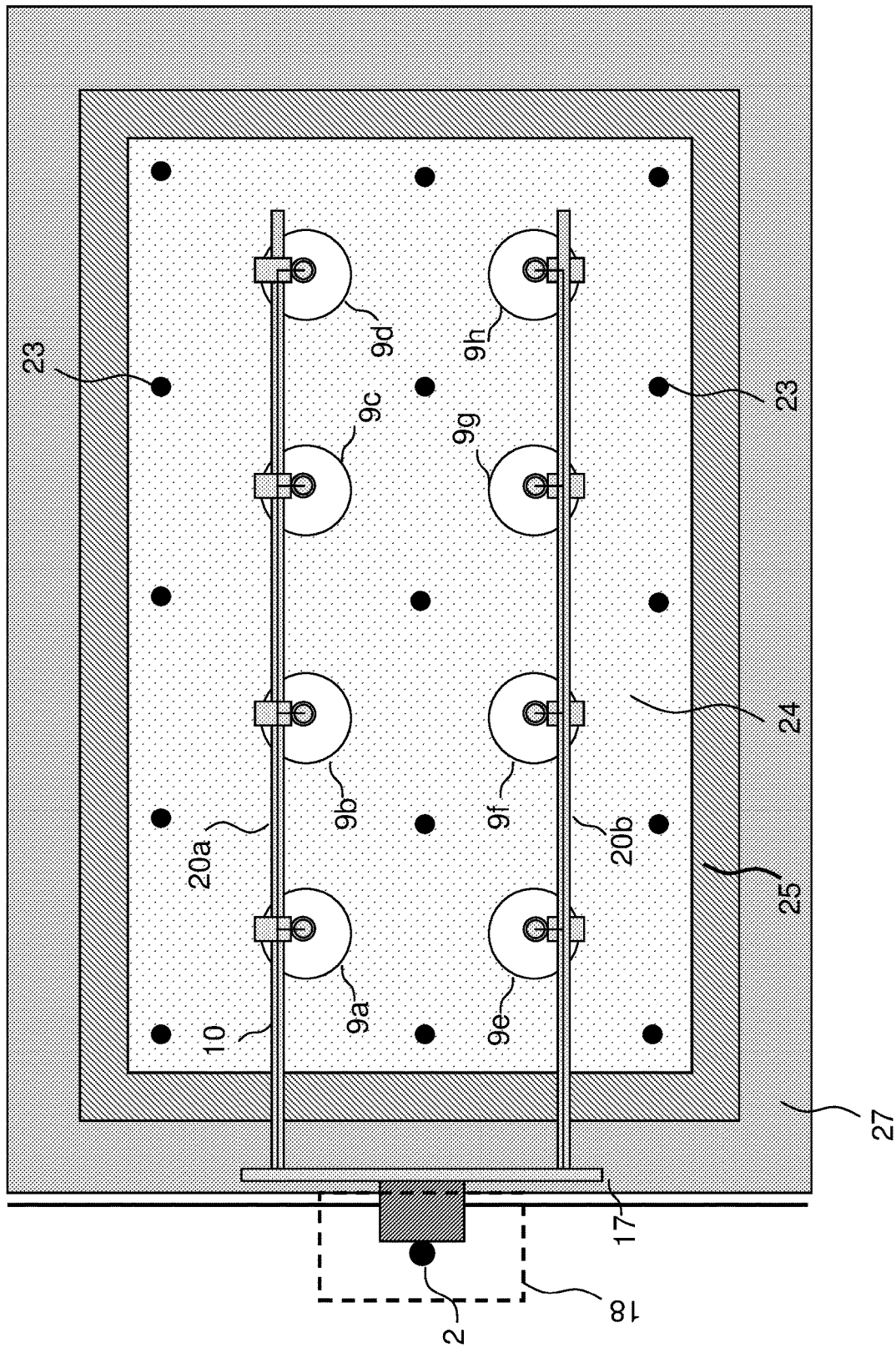
FIG. 6 is an alternative schematic illustration of top view of a 8-channel scanning water analyzer/tensiometer using a heating block with 8 heating cells.

Referring to FIG. 6, which is an alternative schematic illustration of top view of a 8-channel scanning water analyzer/tensiometer, having 8 heating cells (9*a*, 9*b*, 9*c*, 9*d*, 9*e*, 9*f*, 9*g* and 9*h*) and 15 cartridge heaters (23) in a heating block (24), which is surrounded by insulation materials (25). The sensor holder manifest (10) has 2 round bars or tubes (20*a* and 20*b*) working as guides for positioning precisely the 8 sensors. The electrical wires connecting each sensor are tied to and routed along the sensor holder manifest (10) directly to the data acquisition unit (12).

Figure 7:
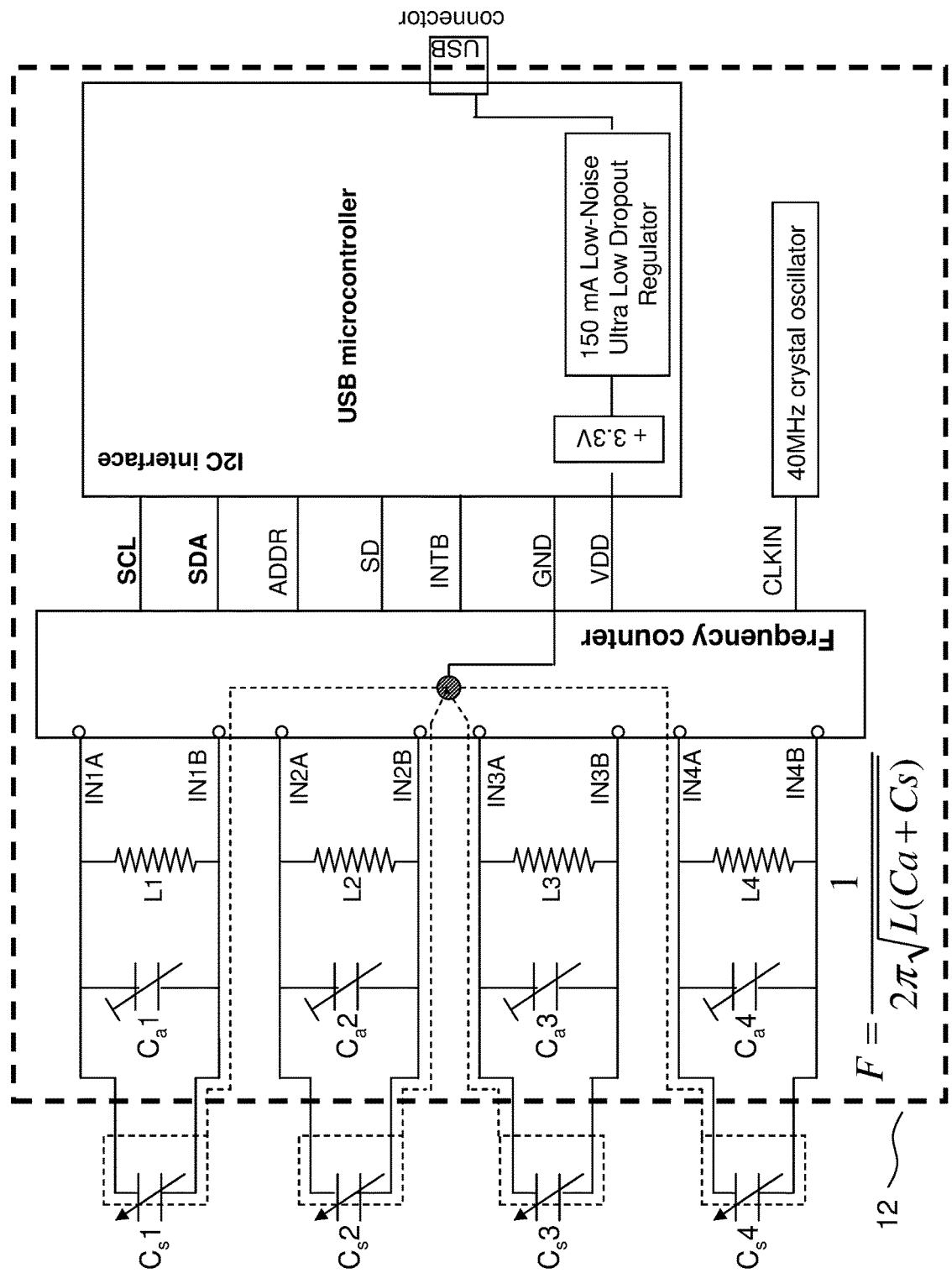
FIG. 7 is a schematic illustration of a 4-channel data acquisition unit.

Referring to FIG. 7, which is a schematic illustration of a 4-channel data acquisition unit (12). It comprises 4 LC-tanks for connecting 4 capacitive sensors, a high precision frequency counter with a multiplexer or a data selector and a USB microcontroller. Each LC tank has an inductor (L) and two capacitors ($C_a$ and $C_s$) connected in parallel to form a resonance circuit. Its resonance frequency (F) can be expressed as $$F = \frac{1}{2\pi\sqrt{L(C_a + C_s)}}, \quad (1)$$

where L is inductance of the inductor, $C_a$ is the capacitance of an adjustable capacitor and $C_s$ is the capacitance of a variable capacitor, which is actually the sensor's capacitance. The resonance frequency is measured using a high precision analog to digital frequency converter or counter having at lease 21-bit resolution, preferably greater than 24-bit resolution and equal or less than 32-bit resolution. The measured frequency is then read by the USB microcontroller unit via different communication interfaces, e.g. I2C, UART, LVDS, SPORT, SPI or PPI, preferably the I2C protocol, which is an inter-integrated circuit. It uses only two lines for communication, a serial data line (SDA) for master and slave to send and receive data, and a serial clock line (SCL) for carrying clock signal. The adjustable capacitors are used to bring all channel's capacitance as close to each other as possible, and it is beneficial to use 4 inductors with inductance value as close to each other as possible, so that the measured frequencies are as close as possible in the beginning of a baseline period. The operating frequency range can be adjusted by using different inductors with different inductance values; the preferable operating frequency range is 800-6000 kHz, in which surrounding noises can be minimized. The high resolution frequency counter has a multiplexer or a data selector, which can be programmed in sequence to measure the frequency of a channel at a time to avoid cross-talking between channels. Each data acquisition unit can support a 4-channel apparatus, and 2 data acquisition units are required to support a 8-channel apparatus. To increase signal stability the inductors and capacitors as well as connecting wires are all shielded and share the same electrical ground (GND) as the frequency counter and the microcontroller. Capacitance of a sensor can be calculated using $$C_s = \left(\frac{1}{L}\right)\left(\frac{1}{2\pi F}\right)^2 - C_a, \quad (2)$$

and its derivative as a function of bottle mark (x or sample volume) is $$C'(x) = \frac{dC_s(x)}{dx} = \frac{dC(x)}{dx}, \quad (3)$$

Figure 8:
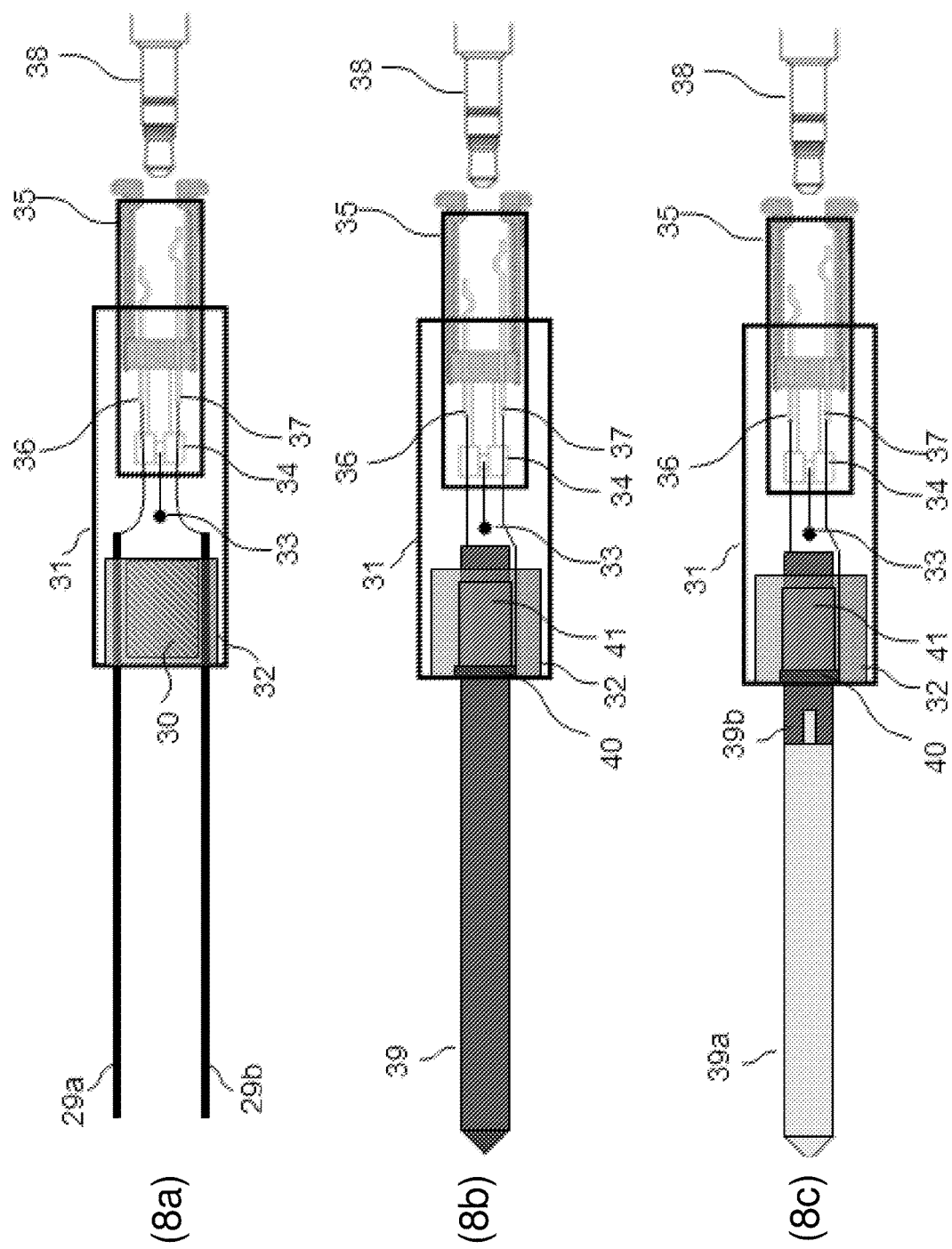
FIG. 8 is a schematic illustration of capacitive sensors: (a) parallel plate sensor, (b) single rod sensor, (c) single rod sensor with detachable sensor head.

Referring to FIG. 8, which is a schematic illustration of capacitive sensors: (a) parallel plate sensor, (b) single rod sensor and (c) single rod sensor with detachable sensor head. The parallel plate sensor (FIG. 8*a*) comprises two stainless steel plates, one as a positive electrode (29*a*), another one as a negative electrode (29*b*). The two plates are spaced with a rectangle column electrical insulation material (30) and center positioned in a stainless steel round tube (31) and firmly attached to its wall using non-conductive epoxy glue (32). The stainless steel round tube also works as a shielding tube and is connected at a point (33) to the shielding conductor (34) of an audio 3-conductor receptacle (35). The positive electrode (29*a*) and the negative electrode (29*b*) are connected to other two conductors (36 and 37) respectively. A stereo audio cable (38) is used to connect the sensor to a channel's connector on the data acquisition unit (12).

The single rod capacitive sensor (FIG. 8*b*) is similar to the parallel plate sensor (FIG. 8*a*) in connecting itself to the audio 3-conductor receptacle (35). The difference is that the positive electrode (29*a*) is replace with a stainless steel rod (39), and the negative electrode (29*b*) is shrunk to a small metal ring (40), which can be copper or stainless steel. The rectangle column electrical insulation material (30) is replaced with a thin film insulation material (41). The parallel plate sensor can provide higher measurement accuracy than the single rod sensor, but the former is a bit inconvenient in cleaning after each test.

The single rod capacitive sensor (FIG. 8*c*) is also similar to the single rod capacitive sensor (FIG. 8*b*) in connecting itself to the audio 3-conductor receptacle (35). The difference is that the positive electrode (39) is split into two parts, the detachable sensor head (39*a*) and the fixed sensor adapter (39*b*); the detachable sensor head (39*a*) is screwed on the fixed sensor body (39*b*) and can be unscrewed for easy cleaning operation; while the fixed sensor adapter (39*b*) is permanently attached to the sensor body.

Figure 9:
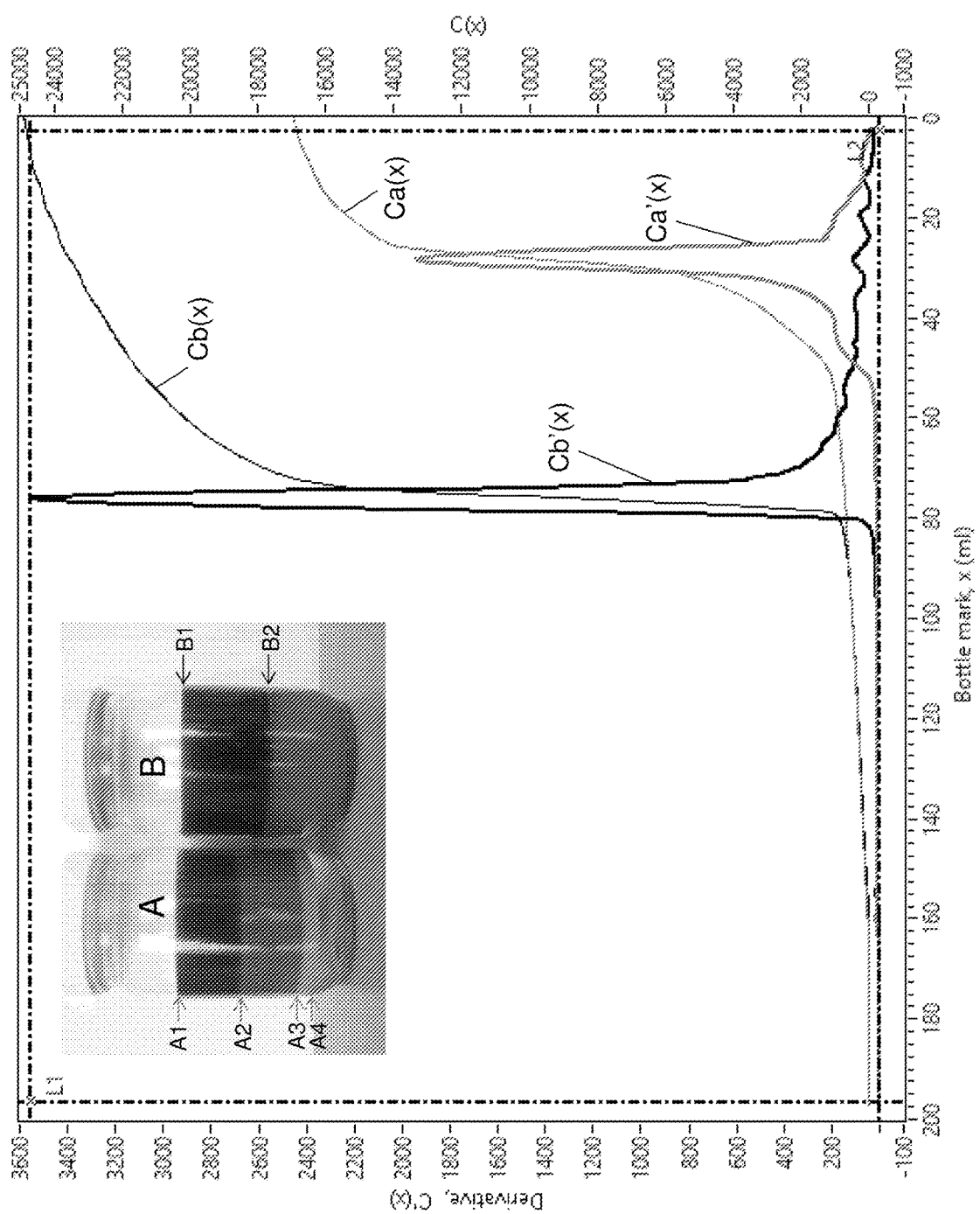
FIG. 9 is an example of scanned curves of capacitance change C(x) and its derivative C'(x) for 2 channels (a full view).

Referring to FIG. 9, which is an example of scanned curves of capacitance C(x) and its derivative C'(x) for 2 channels (for sample bottles A and B), where $C_a(x)$ and $C_b(x)$ are capacitance changes relative to a baseline reference, $C_a'(x)$ and $C_b'(x)$ are derivatives of the capacitance changes for corresponding sample bottles A and B, and x is bottle mark in ml. The equally spaced bottle marks normally represent respective volumes in the middle part, but slightly different from respective volumes at top and bottom parts of a bottle. The derivative, $$C'(x) = \frac{dC(x)}{dx},$$

is derived from C(x) using a moving multiple points polynomial curve fitting. There are 4 phases in bottle A, their interfaces are labelled as A1, A2, A3 and A4 in the inserted photo, where the 4 phases are a clean oil phase between A1 and A2, an emulsion phase between A2 and A3, a rag layer phase between A3 and A4 and an aqueous phase at the bottom. There are only 2 phases in bottle B, their interfaces are labelled as B1 and B2, where the 2 phases are a clean oil phase at the top and an emulsion phase at the bottom.

Figure 10:
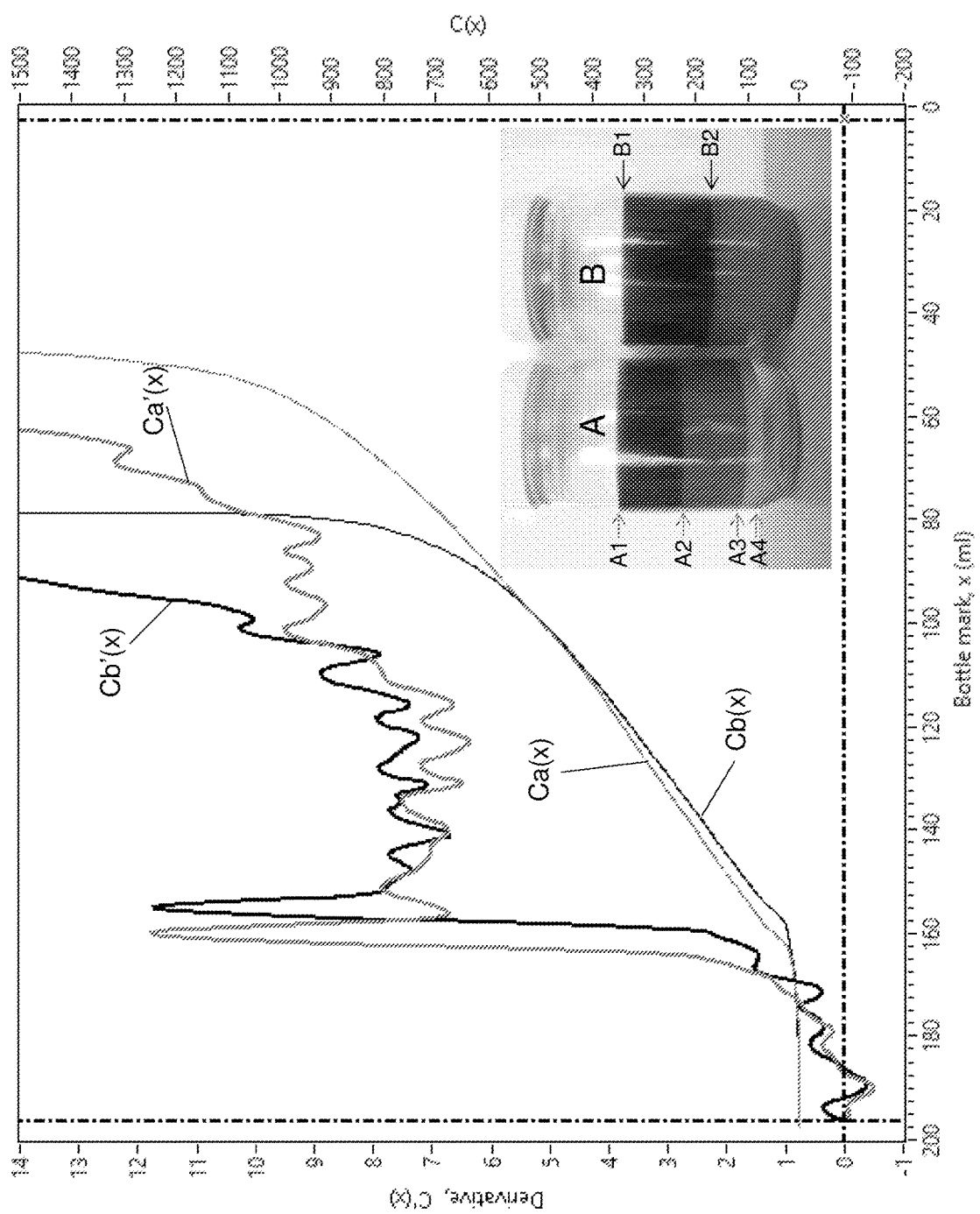
FIG. 10 is an example of the scanned curves of capacitance change C(x) and its derivative C'(x) for 2 channels (a zoom-in view).

Referring to FIG. 10, which is a zoom-in view of the scanned curves of capacitance C(x) and its derivative C'(x) for 2 channels (for sample bottles A and B), all labels share the same meaning as in FIG. 9 for the inserted photo.

Figure 11:
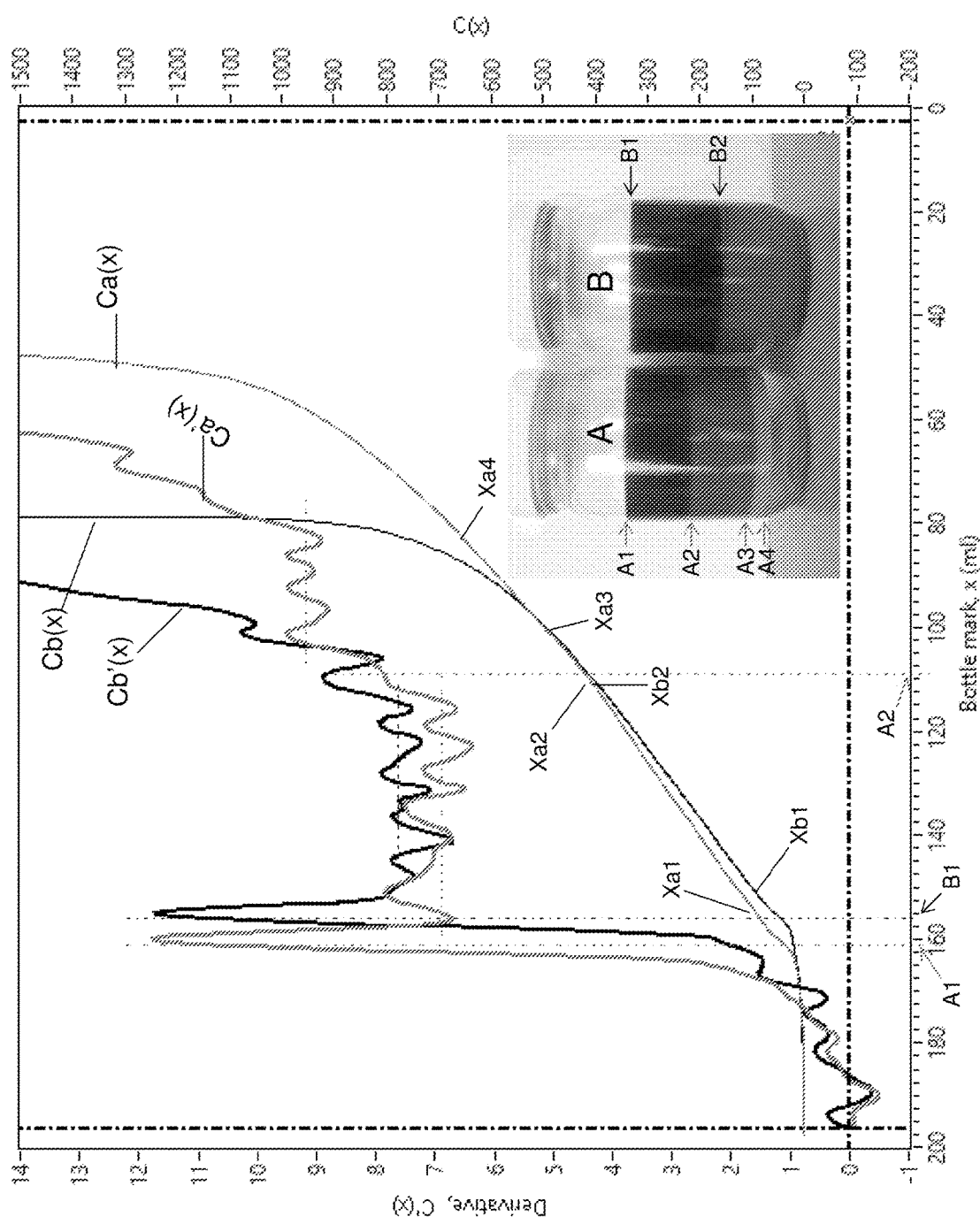
FIG. 11 is an illustration of how to obtain interfacial levels, water contents and interfacial thicknesses from the scanned curves (a zoom-in view).
Figure 12:
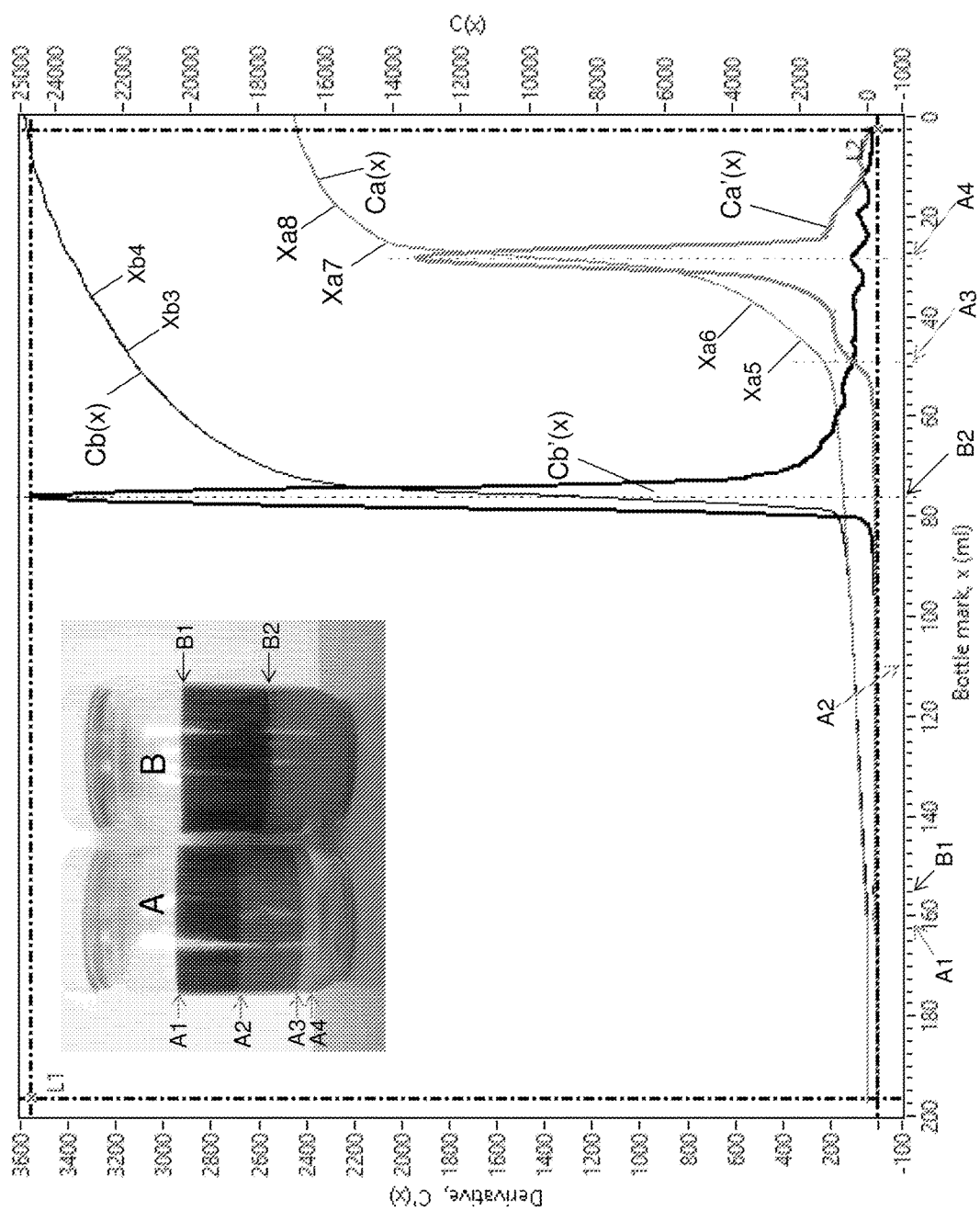
FIG. 12 is an illustration of how to obtain interfacial levels, water contents and interfacial thicknesses from the scanned curves (a full view).

Referring to FIGS. 11 and 12, which are illustrations of how to obtain interfacial levels and water contents from the scanned curves. The derivative C'(x) is advantageous in interfacial level identification as it shows spikes at every interface, denoted using volume in ml starting from bottom of a bottle, e.g. A1 (160.00 ml), A2 (107.90 ml), A3 (48.03 ml) and A4 (28.18 ml) for sample bottle A; B1 (154.70 ml) and B2 (75.89 ml) for sample bottle B. The coordination values [x, C'(x)] are shown simultaneously on the computer screen when the vertical cursor lines are dragged and moved. The water contents in different phases can be obtained from capacitance C(x) curve using linear fitting for specified data ranges that show linear trends. Water content by volume percent, W(x), is proportional to the slope, S(x), of a linear-fitted line, $$W(x) = KS(x) \quad (5),$$

where K is a capacitive coefficient of a testing sample. So, one can have $W_a(x)=K_a S_a(x)$, $W_b(x)=K_b S_b(x)$, etc. where $K_a$ and $K_b$ are the capacitive coefficients of samples A and B respectively, which can be obtained using a calibration curve.

Water content, W(x), is a constant for a linear period of curve C(x), such as all data between bottle mark range (Xa1, Xa2) can be used to derive water content in the top clean oil phase, (Xa3, Xa4) for water content in the emulsion phase, (Xa5, Xa6) for water content in the rag layer and (Xa7, Xa8) for water content in aqueous phase in bottle A; similarly, bottle mark range (Xb1, Xb2) for water content in the top clean oil phase and (Xb3, Xb4) for water content in the emulsion phase in bottle B. A summary of processed data is shown below.

| Sample ID | Phase name | Interfacial level ml | Bottle mark range Label | ml | ml | Slope, S(x) fF/ml |
|---|---|---|---|---|---|---|
| A | Clean oil phase | A1: 160.00 | Xa1, Xa2 | 154.7 | 109.8 | 6.99 |
|   | Emulsion phase | A2: 107.90 | Xa3, Xa4 | 100.7 | 82.3 | 9.17 |
|   | Rag layer phase | A3: 48.03 | Xa5, Xa6 | 44.9 | 38.3 | 182.20 |
|   | Aqueous phase | A4: 28.18 | Xa7, Xa8 | 24.4 | 18.0 | 193.10 |
| B | Clean oil phase | B1: 154.70 | Xb1, Xb2 | 148.4 | 109.8 | 7.50 |
|   | Emulsion phase | B2: 75.89 | Xb3, Xb4 | 47.4 | 35.4 | 93.21 |

It is noted that for chemical ranking, slope, S(x), derived from capacitance value can be directly used without converting it to water content using a calibration curve, because they correlate monotonically and share the same trend. The higher slope value the higher water content in the corresponding phase, such as (1) water content in the clean oil phase is higher in bottle B than in bottle A due to that slope value is higher for the respective phase in bottle B (7.50 fF/ml) than in bottle A (6.99 fF/ml); (2) water content in the emulsion phase is significantly higher in bottle B than in bottle A due to that slope value is higher for the respective phase in bottle B (93.21 fF/ml) than in bottle A (9.17 fF/ml); and (3) water content increases from the clean oil phase through the aqueous phase in bottle A due to that slope values are in an ascending order: 6.99, 9.17, 182.20 and 193.10 fF/ml. This is a very unique feature of present invention in chemical screening tests.

It is also noted that derivative C'(x) has the same meaning as slope value S(x) if the bottle mark x range is narrow enough for linear fitting. Hence, C'(x) curves can be directly used for chemical ranking in a chemical screening test, excluding those spikes for phase boundary identification.

A spike of the derivative C'(x) represents additional capacitance of the respective interface, which is a measure of excess charges, Q, at the interface and can be evaluated using the area of the spike or be calculated directly using capacitance change over the spike, $$Q = C(x2) - C(x1) \quad (6),$$

where x1 and x2 are the onset and offset of the spike. In other words, interfacial thickness, δ, can also be evaluated by $$\delta = x2 - x1 \quad (7).$$

Interfacial thickness can be used as an additional marker for evaluating chemical performance, the greater the interfacial thickness the harder for oil/water phase separation.

Figure 13:
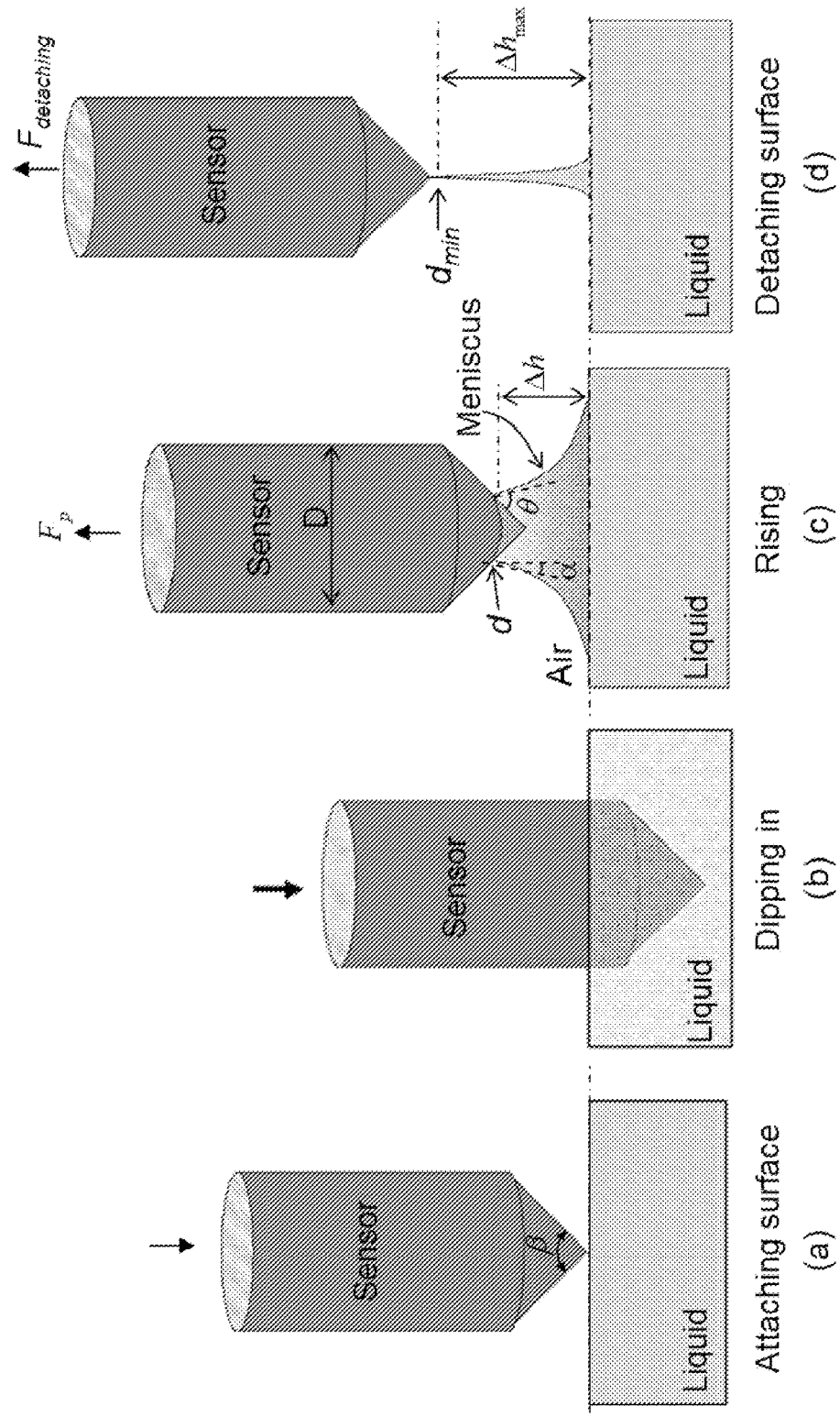
FIG. 13 is an illustration of the surface/interfacial tension measuring process.

Both surface and interfacial tensions can be measured with acceptable accuracy for chemical ranking or chemical selection using the multi-channel scanning water analyzer (MCSWA) directly, which make it a multi-channel tensiometer. The working principle is similar to and a variation of the Du Noüy-Padday rod method. It uses multiple stainless steel rods with a cone-shaped tip as capacitive sensors in conjunction with the MCSWA's fully automated positioning system that can precisely achieve 0.06% accuracy and 0.04 μm resolution. FIG. 13 is an illustration of the surface/interfacial tension measuring process for a single sensor. Multiple sensors are arranged in parallel and automatically controlled for a multi-channel tensiometer, which is a bonus function of the multi-channel scanning water analyzer.

In a measurement scan, the sensors move down from one medium (e.g. the air for surface tension or a liquid for interfacial tension) and dip into another liquid medium and hold in the liquid medium for a short time duration and then rise up to its original position.

During the sensor rising period, the excessive force that needs to pull the sensor up is equal to the weight of the meniscus pulled up above the reference level. The reference level is the flat meniscus before the sensor's contact with the liquid. If the sensor tip is at a distance Δh above the reference level then the excessive vertical pulling force, $F_p$, can be expressed as $$F_p = \pi d \gamma \cos \alpha + V_m(\rho_2 - \rho_1)g, \quad (8)$$

where γ denotes the interfacial tension between the liquid and the surrounding medium, πd denotes the wetted perimeter and d the wetted diameter, and α is the angle between the liquid and the gravity direction, which can be calculated using $$\alpha = \theta - \frac{\beta}{2}, \quad (9)$$

where θ is the contact angle between the liquid and the sensor's cone surface, β is the cone shape angle. The second part of equation (8) represents the net gravitational force excluding the buoyancy, where $V_m$ is the volume of the meniscus pulled up above the reference level, $\rho_1$ and $\rho_2$ are the densities of the two media, g the gravitational acceleration constant.

Considering the cone-shaped sensor tip that makes the meniscus as an elastic thin liquid string during pulling, the gravitational part is a few order of magnitude below the first surface tension part, hence equation (8) can be rewritten as, $$F_p = \pi d\gamma \cos \alpha. \quad (10)$$

Figure 14:
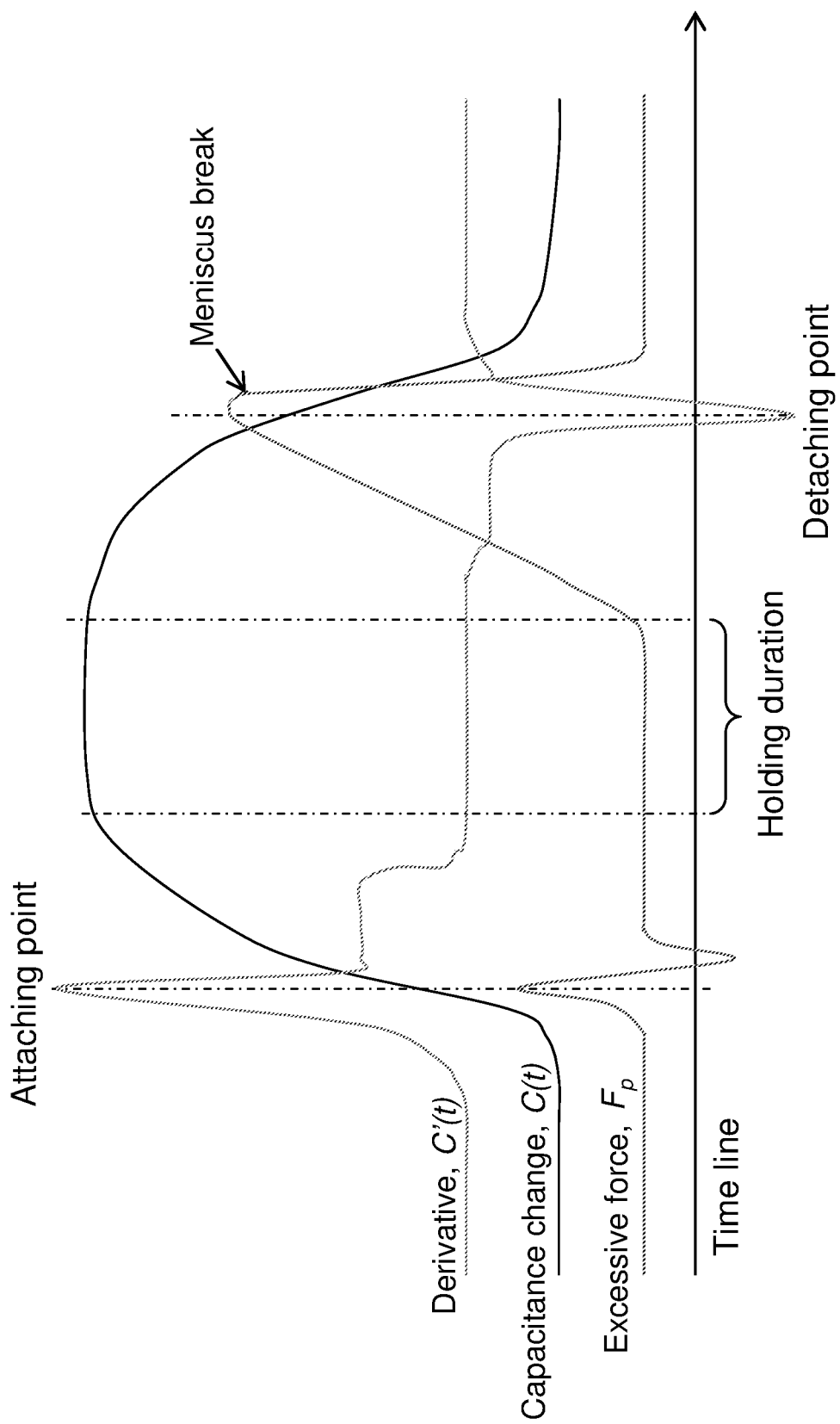
FIG. 14 is an illustration of the response signals representing capacitance change C(x) and its derivative C'(x) as well as inserted excessive pulling force, Fp, as a function of time.

For the sensor rising period, the excessive pulling force on the sensor is approximately proportional to the height of the meniscus as the blue curve shown in FIG. 14, which is an illustration of the response signals representing capacitance change, C(t), and its derivative, C'(t), as well as inserted excessive pulling force, $F_p$, as a function of time.

$$F_p = k\Delta h, \quad (11)$$

where k is a sensor constant.

Combining equations (10) and (11), the excessive pulling force on the sensor at the detaching point, $F_{detaching}$, can be given as below, $$F_{detaching} = \lim_{d \to d_{min}, \alpha \to 0} F_p = \lim_{d \to d_{min}, \alpha \to 0} \pi d\gamma \cos \alpha = \pi d_{min}\gamma = k\Delta h_{max}, \quad (12)$$

where $d_{min}$ is the minimum diameter of the liquid medium relating to the sensor, which is a characteristic of the sensor, depending on the surface roughness and the angle sharpness of the cone-shipped sensor tip. $\Delta h_{max}$ is the maximum height of the meniscus at the minimum wetting diameter, $d_{min}$. The meniscus liquid string will break if the sensor is further pulled up. Rearranging equation (12) the surface tension γ can be obtained, $$\gamma = \frac{k}{\pi d_{min}} \Delta h_{max} \quad (13)$$

$\Delta h_{max}$ can be derived via numerical data processing using recorded capacitance change, C(t), and its derivative function, C'(t). The coefficient, $$\frac{k}{\pi d_{max}},$$

can be obtained using a reference liquid with known surface tension, such as water for aqueous systems, xylene for hydrocarbons.

The capacitance change, C(t), of the sensor shows a sharp increase/decrease at the attaching and detaching points, which are identified by a maximum and a minimum points ($t_{max}$ and $t_{min}$) of its derivative function, C'(t), as illustrated in FIG. 14. Each sensor tip's vertical position at the attaching point, $p(t_{max})$, and the detaching point, $P(t_{min})$, can be obtained numerically via a linear interpolation using recorded tip position function, p(t), $\Delta h_{max}$ can then be found by $$\Delta h_{max} = P(t_{min}) - P(t_{max}). \quad (14)$$

Figure 15:
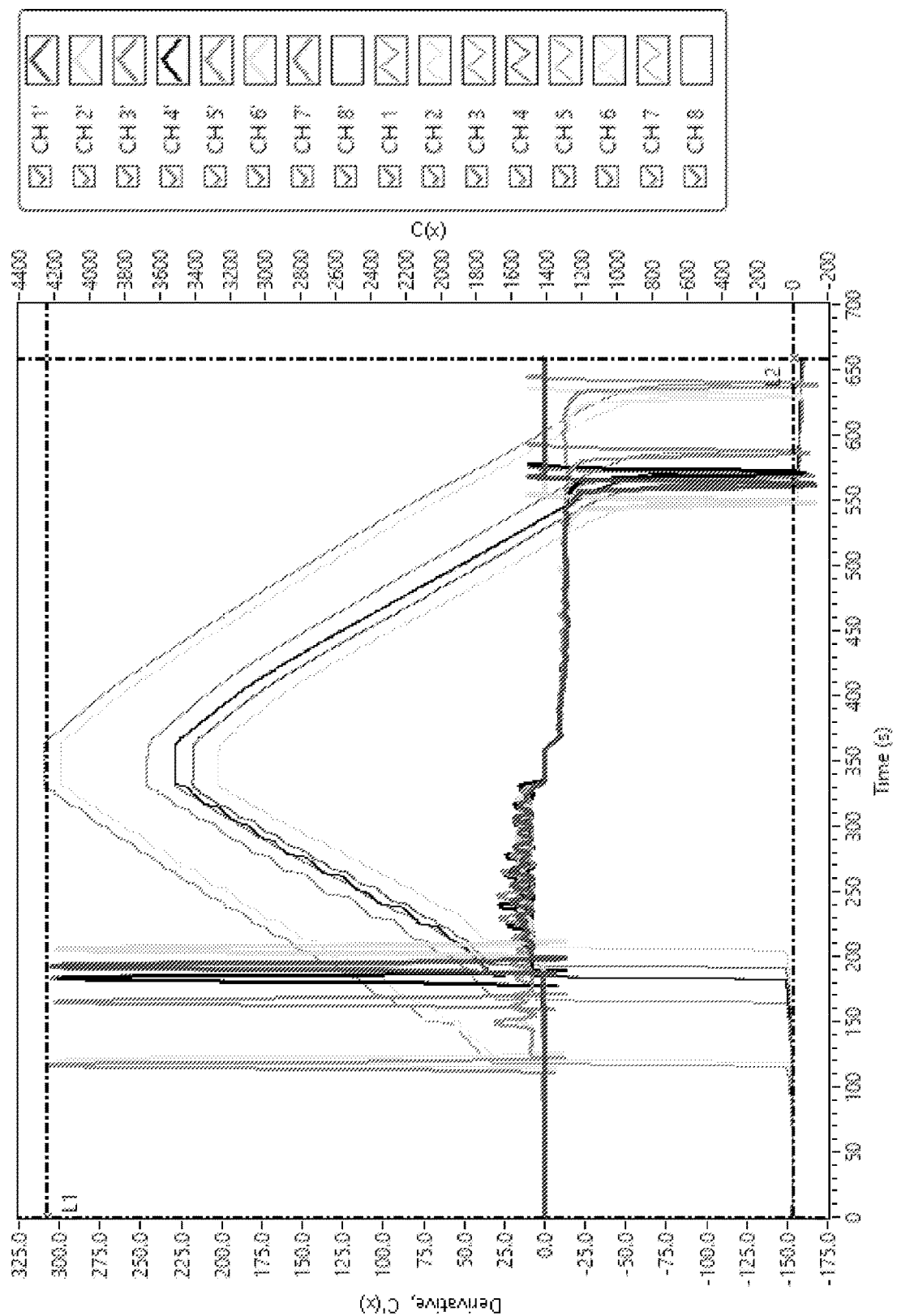
FIG. 15 shows actual scanned curves of capacitance change C(x) and its derivative C'(x) for de-ionized water using a 8-channel tensiometer.
Figure 16:
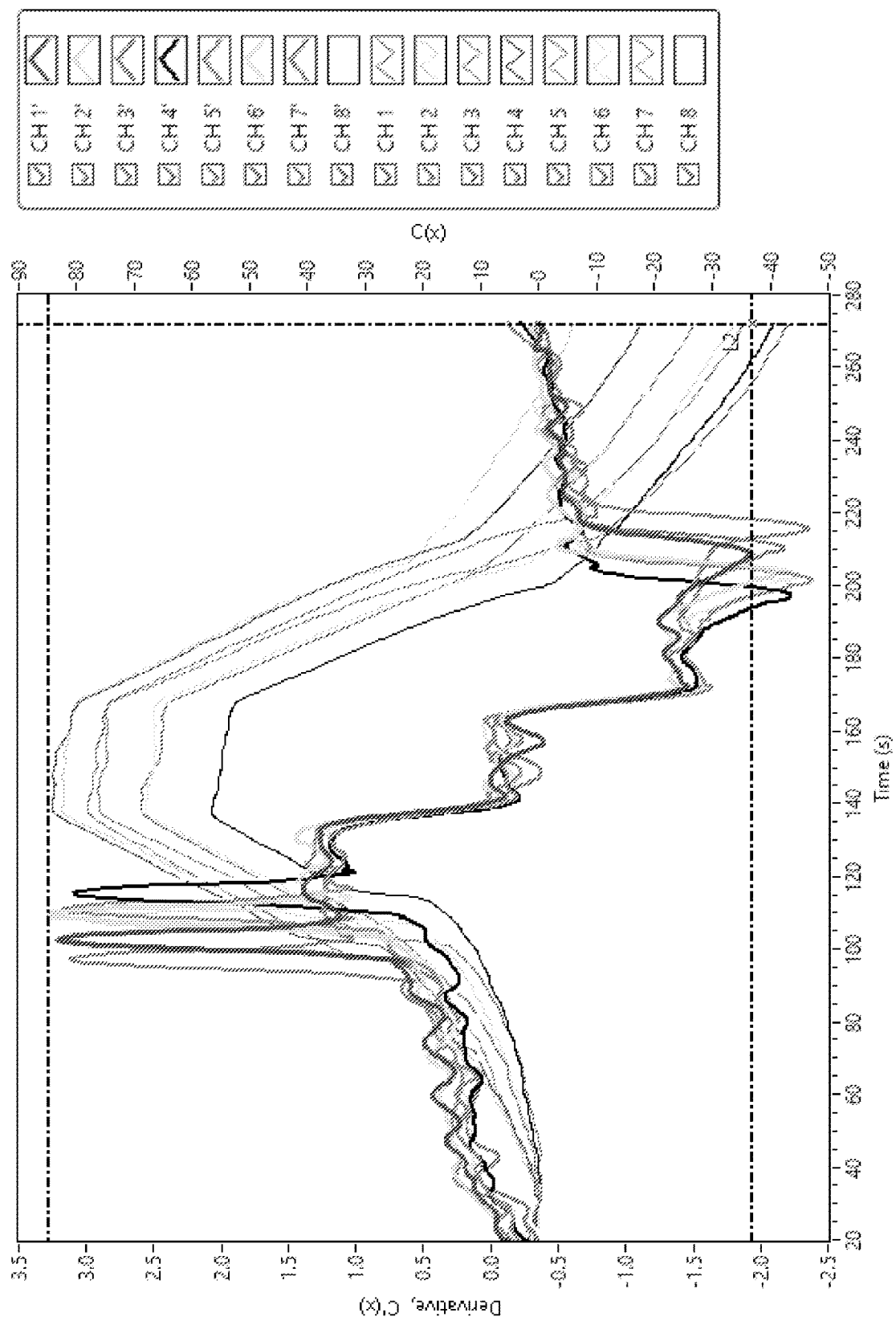
FIG. 16 shows actual scanned curves of capacitance change C(x) and its derivative C'(x) for 0W-20 engine oil using a 8-channel tensiometer.

FIGS. 15 and 16 show the actual scanned curves of capacitance changes, C(t), and its derivative function, C'(t), for de-ionized water and 0W-20 engine oil respectively using a 8-channel tensiometer. Eight surface tension values of 8 samples can be obtained in one test run.

The multi-channel scanning water analyzer or tensiometer is a very compact design making it portable for both lab and field tests. Number of channels can be selectable from 1 up to 16, preferably even numbers. Its multi-function (water content profile analysis, surface and interfacial level identification and tension measurement) make it a cost effective instrument for different applications. The multi-channel scanning measurement makes chemical selection efficiently and environmental friendly. Critical micelle concentration of a surface active agent can be measured in one test run.

The present invention meets the trend of energy digitization.

The invention claimed is:
1. An apparatus comprising
   a support station comprising
      a base frame,
      a post, and
      a clamp,
   a motorized vertical linear stage comprising
      a motor,
      a motor controller,
      a motor travel guide, and
      a moving unit,
   a heating system comprising
      a heating control box, and
      a plurality of heating cells,
   a sensor holder manifest holding a plurality of sensors,
   a data acquisition unit attached to the moving unit so that the data acquisition unit is configured to move with the moving unit,
   a front enclosure,
   a fixed rear enclosure,
   a plurality of glass bottles, each glass bottle containing a respective testing sample, and
   an integrated driver for controlling movement of the moving unit;
   wherein the data acquisition unit comprises a plurality of channels;
   wherein each channel of the plurality of channels is:
      communicatively connected to a respective one of the plurality of sensors; and
      disposed above a respective one of the plurality of glass bottles, and
   wherein each one of the glass bottles is heated by a respective one of the plurality of heating cells.

2. The apparatus of claim 1, wherein the plurality of heating cells are arranged center-symmetrically;
   wherein the sensor holder manifest comprises two round bars or four round bars; and
   wherein the plurality of sensors are hung on the two round bars or the four round bars or via a plurality of ninety-degree adapters.

3. The apparatus of claim 1, wherein each heating cell of the plurality of heating cells comprises three cartridge heaters.

4. The apparatus of claim 1, wherein the plurality of heating cells are grouped into 2 sets.

5. The apparatus of claim 1, wherein the plurality of heating cells and a plurality of cartridge heaters are integrated in a heating block.

6. The apparatus of claim 1, wherein the data acquisition unit comprises a plurality of LC-tanks for connecting a plurality of capacitive sensors.

7. The apparatus of claim 6, wherein the plurality of capacitive sensors are parallel plate sensors, single rod sensors, or single rod sensors with detachable sensor heads.

8. The apparatus of claim 7, wherein the plurality of capacitive sensors are the single rod sensors each having a cone-shaped sensor tip.

9. The apparatus of claim 8, wherein each of the single rod sensors comprises a fixed sensor head adapter and a detachable sensor head.

10. The apparatus of claim 1, wherein the apparatus measures water content profiles, surface or interfacial levels and interfacial thicknesses of multiphase dispersions by simultaneously dipping the respective sensor into the respective testing sample at a preset scanning velocity in a range from 0.1 to 0.2 mm/sec,
wherein scanned curves of capacitance change $C(x)$ and corresponding derivative $C'(x)$ are used to derive the water content profiles, the surface or interfacial levels and the interfacial thicknesses of the multiphase dispersions; and
wherein the corresponding derivative, $C'(x)=dC(x)/dx$, is derived from $C(x)$ using a moving multiple points polynomial curve fitting.

11. The apparatus of claim 1, wherein the apparatus measures surface or interfacial tensions of multiphase dispersions by simultaneously dipping each of the plurality of sensors into respective test samples at a preset scanning velocity in a range from 0.02 to 0.20 mm/s;
wherein a vertical position of a tip of a sensor of the plurality of sensors at an attaching point, $p(t_{max})$, and a detaching point, $P(t_{min})$, is obtained numerically via a linear interpolation using recorded tip position function, $p(t)$;
wherein $\Delta h_{max}$ is determined by the equation $\Delta h_{max}=P(t_{min})-P(t_{max})$;
wherein surface or interfacial tension $\gamma$ is determined by the equation $$\gamma = \frac{k}{\pi d_{min}} \Delta h_{max};$$

and
wherein a coefficient, $$\frac{k}{\pi d_{max}},$$

is determined using a reference liquid with known surface tension.

* * * * *